US007232926B2

(12) United States Patent
Hamprecht et al.

(10) Patent No.: US 7,232,926 B2
(45) Date of Patent: Jun. 19, 2007

(54) METHOD FOR THE PRODUCTION OF SULPHAMIC ACID HALOGENIDES

(75) Inventors: Gerhard Hamprecht, Weinheim (DE); Michael Puhl, Lampertheim (DE); Robert Reinhard, Ludwigshafen (DE); Ingo Sagasser, Dannstadt-Schauernheim (DE); Thomas Schmidt, Neustadt (DE); Norbert Götz, Worms (DE); Thomas Zierke, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 391 days.

(21) Appl. No.: 10/513,668

(22) PCT Filed: May 15, 2003

(86) PCT No.: PCT/EP03/05126

§ 371 (c)(1),
(2), (4) Date: Nov. 8, 2004

(87) PCT Pub. No.: WO03/097589

PCT Pub. Date: Nov. 27, 2003

(65) Prior Publication Data

US 2005/0159622 A1 Jul. 21, 2005

(30) Foreign Application Priority Data

May 16, 2002 (DE) .................. 102 21 910

(51) Int. Cl.
C07C 19/00 (2006.01)
C07D 239/02 (2006.01)

(52) U.S. Cl. ............ 562/822; 544/298; 544/308; 544/311

(58) Field of Classification Search ................. 562/822
See application file for complete search history.

(56) References Cited

U.S. PATENT DOCUMENTS

| 3,992,444 | A | 11/1976 | Hamprecht et al. | 260/543 |
|---|---|---|---|---|
| 4,049,709 | A | 9/1977 | Hamprecht et al. | 260/543 |
| 4,131,620 | A | 12/1978 | Hamprecht | 260/543 |
| 4,260,560 | A | 4/1981 | Jacobs et al. | 260/543 |
| 4,868,308 | A | 9/1989 | Merkle et al. | 546/310 |
| 5,099,025 | A | 3/1992 | Kaufmann et al. | 546/345 |

FOREIGN PATENT DOCUMENTS

| DE | 946 710 | 8/1956 |
|---|---|---|
| DE | 1 028 129 | 4/1958 |
| DE | 12 42 627 | 6/1967 |
| GB | 1 488 186 | 10/1977 |
| GB | 2 038 334 A | 7/1980 |
| WO | WO 98/28280 | 7/1998 |
| WO | WO 00/18770 | 4/2000 |
| WO | WO 01/83459 A2 | 11/2001 |

OTHER PUBLICATIONS

G. Hamprecht, G. Hamprecht et al.—Angew. Chem. 93 (1981), p. 151-163.
Hamprecht, Acta Chem. Scand. 19, (1963), p. 2141.
Henkel, 2001-656760/75.
Warner et al., Bull. Soc. Chim. Belg. 93, 1984, p. 920.
R. Wegler, R. Wegler et al., J. Liebigs Ann. Chem. (1959), 624, p. 25-29.
R. E. Olson, R.E. Olson et al.—J. Med. Chem. (1999), 42, p. 1189.
Sowada, R. Sowada—J. Prakt. Chem.; 33; 1966; p. 240-246 (BRN 2362206).
XP-002253898, Daniel, Joseph; Shukla, Deepti; Dhar, Durga Nath; Chem. Lett; 8; 1992; p. 1575-1578 (BRN 58 147 89).
XP-002253899, K. Clauss et al., Justus Liebigs Ann. Chem.; 1974; p. 561-592 (BRN 1116113).
XP-002253900, Sridhara; Latscha; Z. Naturforsch. B Anorg. Chem. Org. Chem.; 30; 1975; p. 969 (BRN 991720).
XP-002253901, Moriconi; Meyer; Teleay; Tetrahedron Lett.; 1968; p. 3823 BRN 1457235).
XP-002253902, Isaka, Masahiko; Williard, Paul G.; Nakamura, Eiichi, Bull. Chem. Soc. Jpn.; 72, 9; 1999; p. 2115-2116 (BRN 84 03 296).

*Primary Examiner*—Sikarl A. Witherspoon
(74) *Attorney, Agent, or Firm*—Novak Druce & Quigg, LLP

(57) ABSTRACT

The present invention relates to a process for preparing sulfamoyl halides of primary or secondary amines, comprising the following steps:

i) reacting a primary or secondary amine A1 with at least equimolar amounts of $SO_3$ or an $SO_3$ source in the presence of at least equimolar amounts of a tertiary amine A2, based in each case on the amine A1, and ii) reacting the reaction mixture obtained in step i) with at least the amount of a phosphorus halide required by the stoichiometry;

The invention further relates to a process for preparing sulfonic diamides, comprising the preparation of sulfamoyl halides by means of carrying out steps i) and ii) and subsequently reacting the sulfamoyl halide obtained with ammonia. The invention further relates to the use of this process for preparing active herbicidal ingredients having a sulfuric diamide structure. The invention further relates to novel sulfamoyl chlorides.

14 Claims, No Drawings

METHOD FOR THE PRODUCTION OF SULPHAMIC ACID HALOGENIDES

This is a 371 of PCT/EP03/05126, filed May 15, 2003 and published as WO 03/097589 on Nov. 27, 2003.

The invention relates to a process for preparing sulfamoyl halides, in particular sulfamoyl chlorides of primary or in particular secondary amides.

Sulfamoyl halides of primary or secondary amines are interesting intermediates for the preparation of active ingredients having sulfonamide or sulfuric diamide structural units. An overview of alkylsulfamoyl chlorides, their preparation and their use can be found in G. Hamprecht et al. Angew. Chem. 93, (1981), p. 151-163.

In principle, sulfamoyl chlorides may be prepared by reacting monoalkylammonium chlorides with sulfonyl chloride, also referred to hereinbelow as sulfuryl chloride (Acta Chem. Scand. 19, (1963), p. 2141 and also DE-A 1242627). A disadvantage of this process is the long reaction times. In addition, the use of sulfonyl chloride leads to a multiplicity of side reactions. In the case of long-chain amines, for example, the chlorinating action of sulfonyl chloride dominates, so that sulfamyl chlorides of such amines are not accessible by this route.

This process is also utilized in WO 98/28280, WO 00/18770, WO 01/64808 and Bull. Soc. Chim. Belg. 93, 1984, p. 920 for the preparation of N-methoxyethyl-N-methylsulfamoyl chloride, N-cyanoethyl-N-methylsulfamoyl chloride, N-allyl-N-methyl-sulfamoyl chloride and bis-N-allylsulfamoyl chloride. The yields found are generally low.

DE-A 2164176 and EP-A 11794 disclose processes for preparing sulfamoyl halides of the formula R—NH—SO$_2$X, where R is an aliphatic or cycloaliphatic radical and X is a halogen atom by reacting a sulfamic acid of the general formula R—NH—SO$_3$H where R is as defined above with an acid halide of phosphorus. The sulfamic acids used as starting materials are prepared by reacting isocyanates R—N=C=O with sulfuric acid or by reacting disubstituted ureas with oleum. One disadvantage of these processes is that they start from comparatively expensive starting products whose preparation is costly and inconvenient. In addition, as a consequence of the reaction conditions necessary for the preparation of the sulfamic acids (sulfuric acid or oleum), this process is suitable only for the preparation of those sulfamoyl halides which bear a comparatively inert hydrocarbon radical on the nitrogen. This process is unsuitable for the preparation of sulfamoyl halides which have reactive groups, for example olefinic double bonds or triple bonds, cyanoalkyl groups, alkoxyalkyl groups or aldehydic carbonyl groups.

R. Wegler et al. in J. Liebigs Ann. Chem. (1959), 624, p. 25-29 describe the preparation of N,N-dialkylsulfamoyl chlorides by initially converting the secondary amines or their hydrochlorides by treatment with chlorine to the N-chloroamines which are then converted by reaction with sulfur dioxide in the presence of chlorine to the sulfamoyl chlorides. An alternative described is the reaction of dialkylamines with sulfur dioxide in carbon tetrachloride with subsequent reaction of the resulting thioamidic acids with chlorine to give the sulfamoyl chlorides. A disadvantage of both processes is the use of elemental chlorine, which limits the process to those amines which have no groups reactive towards chlorine. Also, the intermediate generated in the first process variants is a very unstable N-chloroamine which is very problematic in its handling.

The German patent 946710 describes the preparation of sulfamoyl chlorides by reacting carbamoyl chlorides with sulfur trioxide.

R. E. Olson et al., J. Med. Chem. (1999), 42, p. 1189 describe the preparation of isobutylsulfamoyl chloride from isobutylamine by initially reacting isobutylamine with chlorosulfonic acid and reacting the resulting isobutylammonium salt of isobutylsulfamic acid with phosphorus pentachloride. However, the yields obtained are not satisfactory.

Although a multiplicity of processes for preparing sulfamoyl chlorides is known from the prior art, no efficient process for preparing sulfamoyl chlorides has yet been provided which is not restricted to the preparation of sulfamoyl chlorides of inert amines which have none of the abovementioned reactive groups, and which allows the amines to be used directly as starting materials.

It is an object of the present invention to provide such a process.

We have found that this object is achieved, surprisingly, by a process in which a primary or secondary amine is initially reacted with at least equimolar amounts of sulfur trioxide or a sulfur trioxide source in the presence of at least equimolar amounts of a tertiary amine A2 and the resulting ammonium sulfamate is reacted with at least the amount of a phosphorus halide required by the stoichiometry.

The present invention therefore relates to a process for preparing sulfamoyl halides of primary or secondary amines, comprising the following steps:

i) reacting a primary or secondary amine A1 with at least equimolar amounts of SO$_3$ or an SO$_3$ source in the presence of at least equimolar amounts of a tertiary amine A2, based in each case on the amine A1, and ii) reacting the reaction mixture obtained in step i) with at least the amount of a phosphorus halide required by the stoichiometry.

The process according to the invention is best described by the reaction equation shown in scheme 1.

Scheme 1:

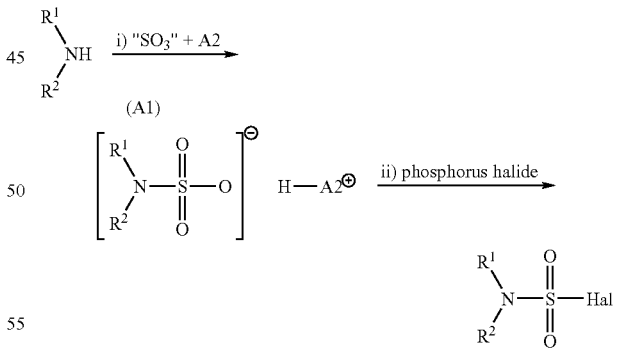

In scheme 1, R$^1$R$^2$—NH represents a primary or secondary amine, A1, A2 represents a tertiary amine and Hal represents a halogen atom which has been transferred from a phosphorus halide.

Examples of suitable primary or secondary amines are those of the formulae IA and IB $$R^1—NH_2 \quad (IA);$$

$$R^1R^2N—H \quad (IB),$$

where $R^1$ and $R^2$ are each independently $C_1$-$C_{20}$-alkyl, $C_2$-$C_{20}$-alkenyl or $C_2$-$C_{20}$-alkynyl, each of which may be unsubstituted or substituted by CN, $NO_2$, $C_1$-$C_4$-alkoxy, $C_1$-$C_4$-alkylthio, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, phenyl which may itself have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro or cyano, $C_1$-$C_{20}$-haloalkyl, $C_2$-$C_{20}$-haloalkenyl, $C_2$-$C_{20}$-haloalkynyl, $C_3$-$C_{10}$-cycloalkyl, $C_5$-$C_{10}$-cycloalkenyl, heterocyclyl having from one to 3 heteroatoms selected from O, S and N, phenyl or naphthyl, where heterocyclyl, phenyl or naphthyl may themselves have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro or cyano, $R^1$ and $R^2$ together may also form a saturated or partially unsaturated 5- to 8-membered nitrogen heterocycle which may itself be substituted by $C_1$-$C_4$-alkyl, $C_1$-$C_4$-alkoxy and/or $C_1$-$C_4$-haloalkyl, and have one or 2 carbonyl groups or thiocarbonyl groups and/or one or two further heteroatoms selected from O, S and N as ring members.

The organic molecular moieties specified here and hereinbelow for the substituents or as radicals of phenyl and heterocyclyl radicals represent collective terms for individual listings of the individual group members, and the expression $C_n$-$C_m$ specifies the possible number of carbon atoms in the molecular moiety. All hydrocarbon chains, i.e. all alkyl, alkenyl and alkynyl moieties, may be straight-chain or branched. Unless stated otherwise, halogenated substituents preferably bear from one to six identical or different halogen atoms. The definition of halogen in each case is fluorine, chlorine, bromine or iodine.

Examples of specific definitions include:

$C_1$-$C_4$-alkyl: for example methyl, ethyl, propyl, 1-methylethyl, butyl, 1-methylpropyl, 2-methylpropyl or 1,1-dimethylethyl;

$C_1$-$C_{20}$-alkyl: a saturated aliphatic hydrocarbon radical having from 1 to 20 carbon atoms and in particular having from 1 to 10 carbon atoms ($C_1$-$C_{10}$-alkyl), e.g. $C_1$-$C_4$-alkyl, as specified above, and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, n-heptyl, n-nonyl, n-decyl, 1-methylhexyl, 1-ethylhexyl, 1-methylheptyl, 1-methyloctyl, 1-methylnonyl, n-undecyl, 1-ethylnonyl, 2-ethylnonyl, 1,2-dimethylnonyl, n-dodecyl, 1-methylundecyl, 1-ethyldecyl, n-tridecyl, 1-methyldodecyl, 1-ethylundecyl, n-tetradecyl, 1-methyltridecyl, 1-ethyldodecyl, n-Pentadecyl, 1-methyltetradecyl, 1-ethyltridecyl, n-hexadecyl, 1-methylpentadecyl, 1-ethyltetradecyl, n-heptadecyl, 1-methylhexadecyl, 1-ethylpentadecyl, n-octadecyl, 1-methylheptadecyl, 1-ethylhexadecyl, n-nonadecyl, 1-methyloctadecyl, n-eicosyl, 1-methylnonadecyl;

$C_2$-$C_{20}$-alkenyl: a monounsaturated olefinic hydrocarbon radical having from 2 to 20 carbon atoms, preferably from 2 to 10 and in particular from 3 to 6 carbon atoms ($C_2$-$C_{10}$-alkenyl and $C_3$-$C_6$-alkenyl), for example ethenyl, prop-2-en-1-yl(=allyl), prop-1-en-1-yl, but-1-en-4-yl, but-2-n-1-yl, but-3-en-1-yl, 1-methylprop-2-en-1-yl, 2-methylprop-2-en-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, 1-ethylprop-1-en-2-yl, n-hex-1-en-1-yl, n-hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-2-en-1-yl, hept-2-en-1-yl, oct-2-en-1-yl, non-2-en-1-yl, dec-2-en-1-yl, undec-2-en-1-yl, dodec-2-en-1-yl, tridec-2-en-1-yl, tetradec-2-en-1-yl, pentadec-2-en-1-yl, hexadec-2-en-1-yl, heptadec-2-en-1-yl, octadec-2-en-1-yl, nonadec-2-en-1-yl, eicosa-2-en-1-yl;

$C_2$-$C_{20}$-alkynyl: a hydrocarbon radical having from 2 to 20 carbon atoms, preferably from 2 to 10 and in particular from 3 to 6 carbon atoms and a triple bond ($C_2$-$C_{10}$-alkynyl and $C_3$-$C_6$-alkynyl), for example, ethynyl, prop-2-yn-1-yl(=propargyl), prop-1-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl, 4-methylpent-2-yn-5-yl, hept-2-yn-1-yl, oct-2-yn-1-yl, non-2-yn-1-yl, dec-2-yn-1-yl, undec-2-yn-1-yl, dodec-2-yn-1-yl, tridec-2-yn-1-yl, tetradec-2-yn-1-yl, pentadec-2-yn-1-yl, hexadec-2-yn-1-yl, heptadec-2-yn-1-yl, octadec-2-yn-1-yl, nonadec-2-yn-1-yl, eicosa-2-yn-1-yl, $C_1$-$C_4$-haloalkyl: a $C_1$-$C_4$-alkyl radical, as specified above, which is partly or fully substituted by fluorine, chlorine, bromine and/or iodine, i.e., for example, choromethyl, dichoromethyl, trichoromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(choromethyl)-2-chloroethyl, 1-(bromomethyl)-2-bromoethyl, 4-fluorobutyl, 4-chlorobutyl, 4-bromobutyl or nonafluorobutyl;

$C_1$-$C_{20}$-haloalkyl: $C_1$-$C_{20}$-alkyl, in particular $C_1$-$C_{10}$-alkyl, as specified above where some or all and in particular from 1 to 6 hydrogen atoms are substituted by halogen atoms, preferably by fluorine and/or chlorine, for example $C_1$-$C_4$-haloalkyl as specified above, and also 5-fluoropentyl, 5-chloropentyl, 5-bromopentyl, 5-iodopentyl, undecafluorpentyl, 6-fluorohexyl, 6-chlorohexyl, 6-bromohexyl, 6-iodohexyl or dodecafluorohexyl;

$C_2$-$C_{20}$-haloalkenyl: $C_2$-$C_{20}$-alkenyl, in particular $C_2$-$C_{10}$-alkenyl, as specified above where some or all and in particular from 1 to 6 hydrogen atoms are substituted by halogen atoms, preferably by fluorine and/or chlorine;

$C_2$-$C_{20}$-haloalkynyl: $C_2$-$C_{20}$-alkynyl, in particular $C_2$-$C_{10}$-alkynyl, as specified above where some or all and in particular from 1 to 6 hydrogen atoms are substituted by halogen atoms, preferably by fluorine and/or chlorine;

$C_3$-$C_{10}$-cycloalkyl: a cycloaliphatic radical having from 3 to 10 carbon atoms, for example cyclopropyl, cyclobutyl, cyclopentyl, cyclohexyl, cycloheptyl, cyclooctyl, cyclononyl or cyclodecyl;

$C_5$-$C_{10}$-cycloalkenyl: a cycloaliphatic radical having from 5 to 10 carbon atoms, preferably from 5 to 8 carbon atoms, and a double bond, for example cyclopenten-1-yl, cyclohexen-1-yl, cyclohepten-1-yl, cycloocten-1-yl, cyclononen-1-yl, cyclodecen-1-yl, cyclopent-2-en-1-yl, cyclohex-2-en-1-yl, cyclohept-2-en-1-yl, cyclooct-2-en-1-yl, cyclonon-2-en-1-yl, cyclodec-2-en-1-yl, cyclohex-3-en-1-yl, cyclohept-3-en-1-yl, cyclooct-3-en-1-yl, cyclooct-4-en-1-yl, cyclonon-3-en-1-yl, cyclonon-4-en-1-yl, cyclodec-4-en-1-yl or cyclodec-3-en-1-yl;

$C_1$-$C_{10}$-cyanoalkyl: $C_1$-$C_{10}$-alkyl substituted by a CN group, for example cyanomethyl, 1-cyanoethyl, 2-cyanoethyl, 1-cyanopropyl, 2-cyanopropyl, 3-cyanopropyl, 1-cyanoprop-2-yl, 2-cyanoprop-2-yl, 1-cyanobutyl, 2-cyanobutyl, 3-cyanobutyl, 4-cyanobutyl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 3-cyano-2,2-dimethylpropyl, 6-cyanohex-1-yl, 7-cyanohept-1-yl, 8-cyanooct-1-yl, 9-cyanonon-1-yl, 10-cyanodec-1-yl;

$C_1$-$C_4$-alkylcarbonyl: an alkyl radical having from 1 to 4 carbon atoms and bonded via a carbonyl group, for example acetyl, propionyl, butyryl or isobutyryl;

($C_1$-$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

di($C_1$-$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)-aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

$C_1$-$C_4$-alkoxy: an alkyl radical having from 1 to 4 carbon atoms and bonded via an oxygen atom, for example methoxy, ethoxy, propoxy, 1-methylethoxy, butoxy, 1-methylpropoxy, 2-methylpropoxy or 1,1-dimethylethoxy;

$C_1$-$C_4$-alkylthio ($C_1$-$C_4$-alkylsulfanyl: $C_1$-$C_4$-alkyl-S—): an alkyl radical having from 1 to 4 carbon atoms and bonded via a sulfur atom, for example methylthio, ethylthio, propylthio, 1-methylethylthio, butylthio, 1-methylpropylthio, 2-methylpropylthio or 1,1-dimethylethylthio;

$C_1$-$C_4$-alkylsulfinyl ($C_1$-$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$-$C_4$-alkylsulfonyl ($C_1$-$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl.

The term heterocyclyl encompasses saturated, partially unsaturated and also aromatic heterocyclic radicals.

Examples of aromatic heterocyclyl include 2- and 3-thienyl, 2- and 3-furyl, 2- and 3-pyrrolyl, 1-, 3- or 4-pyrazolyl, 2-, 3- or 4-pyridinyl, 2- or 4-oxazolyl and the like.

Examples of saturated and partially unsaturated 5- to 8-membered heterocyclic nitrogen radicals which may have one or 2 carbonyl groups, thiocarbonyl groups and/or one or two further heteroatoms selected from O, S and N as ring members include pyrrolidin-1-yl, 1,3-oxazolidin-3-yl, 1,2-oxazolidin-2-yl, 4,5-dihydropyrazol-1-yl, tetrahydropyrazol-1-yl, piperidin-1-yl, morpholin-4-yl, 2-methylmorpholin-4-yl, 3-methylmorpholin-4-yl, 2,6-dimethylmorpholin-4-yl, hexahydropyridazin-1-yl, hexahydropyrimidin-1-yl, hexahydropiperazin-1-yl, hexahydro-1,3,5-triazin-1-yl, hexahydroazepin-1-yl, hexahydro-1,3-diazepin-1-yl, hexahydro-1,4-diazepin-1-yl.

Preferred amines are secondary amines, i.e. $R^1$ and $R^2$ are each different to hydrogen. The amines A1 preferably have only one primary or one secondary amino group. The amines A1 preferably have no alcoholic hydroxyl groups.

Preferred substituents $R^1$ and $R^2$ are each independently selected from $C_1$-$C_{10}$-alkyl, $C_3$-$C_{10}$-alkenyl and $C_3$-$C_{10}$-alkynyl, where the double or triple bond is not attached directly to the carbon atom to which the nitrogen atom is bonded. Preference is further given to $C_1$-$C_4$-alkoxyalkyl, $C_1$-$C_4$-alkylthio-$C_1$-$C_4$-alkyl, cyano-$C_1$-$C_4$-alkyl, $C_5$-$C_8$-cycloalkyl, $C_5$-$C_8$-cycloalkynyl and phenyl which may be substituted in the manner described above and in particular by halogen or $C_1$-$C_4$-alkoxy. Preferably, the radicals $R^1$ and $R^2$ are not both optionally substituted phenyl, naphthyl or heterocyclyl.

In preferred embodiments, $R^1$ and $R^2$ together with the nitrogen atom to which they are bonded are a saturated or partially unsaturated 5- or 6-membered nitrogen heterocycle which may be substituted in the manner described above, in particular 2,5-dihydropyrrol-1-yl, 2,3-dihydropyrrol-1-yl, 1-pyrrolidinyl, 1-piperidinyl, 4-morpholinyl, 2-methylmorpholin-4-yl, 2,6-dimethylmorpholin-4-yl, 1-methylpiperazin-4-yl.

Examples of suitable amines A1 are the amines of the formula $NR^1R^2$ specified in the following table, where the radicals $R^1$ and $R^2$ are each as defined in one row of Table 1:

TABLE 1

| $R^1$ | $R^2$ |
|---|---|
| $CH_3$ | $CH_3$ |
| $CH_3$ | $C_2H_5$ |
| $CH_3$ | $CH(CH_3)_2$ |
| $CH_3$ | $CH_2CH=CH_2$ |
| $CH_3$ | $CH_2CH_2CN$ |
| $CH_3$ | $CH_2CH_2CH_2CN$ |
| $CH_3$ | $CH(CH_3)CH_2CN$ |
| $CH_3$ | $CH_2CH(CH_3)CN$ |
| $CH_3$ | $CH_2C\equiv CH$ |
| $CH_3$ | $C_6H_5$ |
| $CH_3$ | $2\text{-Br}-C_6H_4$ |
| $CH_3$ | $3\text{-Br}-C_6H_4$ |
| $CH_3$ | $4\text{-Br}-C_6H_4$ |
| $CH_3$ | $2\text{-Cl}-C_6H_4$ |
| $CH_3$ | $3\text{-Cl}-C_6H_4$ |
| $CH_3$ | $4\text{-Cl}-C_6H_4$ |
| $CH_3$ | $c\text{-}C_3H_5$ |
| $CH_3$ | $c\text{-}C_5H_9$ |
| $CH_3$ | $c\text{-}C_6H_{11}$ |
| $CH_3$ | $c\text{-}C_7H_{13}$ |
| $CH_3$ | $c\text{-}C_8H_{15}$ |
| $CH_3$ | $CH_2CH=CHCH_3$ |
| $CH_3$ | $CH(CH_3)C_2H_5$ |
| $CH_3$ | $CH_2CH(CH_3)_2$ |
| $CH_3$ | $CH_2CH_2CH_2Cl$ |
| $CH_2CH_3$ | $CH_3$ |
| $CH_2CH_3$ | $C_2H_5$ |
| $CH_2CH_3$ | $CH(CH_3)_2$ |
| $CH_2CH_3$ | $CH_2CH=CH_2$ |
| $CH_2CH_3$ | $CH_2CH_2CN$ |
| $CH_2CH_3$ | $CH_2CH_2CH_2CN$ |
| $CH_2CH_3$ | $CH(CH_3)CH_2CN$ |
| $CH_2CH_3$ | $CH_2CH(CH_3)CN$ |
| $CH_2CH_3$ | $CH_2C\equiv CH$ |
| $CH_2CH_3$ | $C_6H_5$ |
| $CH_2CH_3$ | $2\text{-Br}-C_6H_4$ |
| $CH_2CH_3$ | $3\text{-Br}-C_6H_4$ |
| $CH_2CH_3$ | $4\text{-Br}-C_6H_4$ |
| $CH_2CH_3$ | $2\text{-Cl}-C_6H_4$ |
| $CH_2CH_3$ | $3\text{-Cl}-C_6H_4$ |
| $CH_2CH_3$ | $4\text{-Cl}-C_6H_4$ |
| $CH_2CH_3$ | $c\text{-}C_3H_5$ |
| $CH_2CH_3$ | $c\text{-}C_5H_9$ |
| $CH_2CH_3$ | $c\text{-}C_6H_{11}$ |
| $CH_2CH_3$ | $c\text{-}C_7H_{13}$ |
| $CH_2CH_3$ | $c\text{-}C_8H_{15}$ |
| $CH_2CH_3$ | $CH_2CH=CHCH_3$ |
| $CH_2CH_2CH_3$ | $C_2H_5$ |
| $CH_2CH_2CH_3$ | $CH(CH_3)_2$ |
| $CH_2CH_2CH_3$ | $CH_2CH=CH_2$ |
| $CH_2CH_2CH_3$ | $CH_2CH_2CN$ |
| $CH_2CH_2CH_3$ | $CH_2CH_2CH_2CN$ |
| $CH_2CH_2CH_3$ | $CH(CH_3)CH_2CN$ |
| $CH_2CH_2CH_3$ | $CH_2CH(CH_3)CN$ |
| $CH_2CH_2CH_3$ | $CH_2C\equiv CH$ |
| $CH_2CH_2CH_3$ | $C_6H_5$ |
| $CH_2CH_2CH_3$ | $2\text{-Br}-C_6H_4$ |
| $CH_2CH_2CH_3$ | $3\text{-Br}-C_6H_4$ |
| $CH_2CH_2CH_3$ | $4\text{-Br}-C_6H_4$ |
| $CH_2CH_2CH_3$ | $2\text{-Cl}-C_6H_4$ |
| $CH_2CH_2CH_3$ | $3\text{-Cl}-C_6H_4$ |
| $CH_2CH_2CH_3$ | $4\text{-Cl}-C_6H_4$ |
| $CH_2CH_2CH_3$ | $CH_2CH=CHCH_3$ |
| $CH(CH_3)_2$ | $CH_3$ |
| $CH(CH_3)_2$ | $C_2H_5$ |
| $CH(CH_3)_2$ | $CH(CH_3)_2$ |
| $CH(CH_3)_2$ | $CH_2CH=CH_2$ |
| $CH(CH_3)_2$ | $CH_2CH_2CN$ |
| $CH(CH_3)_2$ | $CH_2CH_2CH_2CN$ |
| $CH(CH_3)_2$ | $CH(CH_3)CH_2CN$ |
| $CH(CH_3)_2$ | $CH_2CH(CH_3)CN$ |
| $CH(CH_3)_2$ | $CH_2CH=CHCH_3$ |
| $CH(CH_3)_2$ | $CH_2C\equiv CH$ |
| $CH(CH_3)_2$ | $C_6H_5$ |
| $CH(CH_3)_2$ | $2\text{-Br}-C_6H_4$ |
| $CH(CH_3)_2$ | $3\text{-Br}-C_6H_4$ |
| $CH(CH_3)_2$ | $4\text{-Br}-C_6H_4$ |
| $CH(CH_3)_2$ | $2\text{-Cl}-C_6H_4$ |
| $CH(CH_3)_2$ | $3\text{-Cl}-C_6H_4$ |
| $CH(CH_3)_2$ | $4\text{-Cl}-C_6H_4$ |
| $CH_2CH=CH_2$ | $CH_2CH_2CN$ |
| $CH_2CH=CH_2$ | $CH_2CH_2CH_2CN$ |
| $CH_2CH=CH_2$ | $CH(CH_3)CH_2CN$ |
| $CH_2CH=CH_2$ | $CH_2CH(CH_3)CN$ |
| $H_5C_2OCH_2CH_2$ | $CH_3$ |
| $H_5C_2OCH_2CH_2$ | $C_2H_5$ |
| $H_5C_2OCH_2CH_2$ | $CH(CH_3)_2$ |
| $H_5C_2OCH_2CH_2$ | $CH_2CH=CH_2$ |
| $H_5C_2OCH_2CH_2$ | $CH_2CH_2CN$ |
| $H_5C_2OCH_2CH_2$ | $CH_2CH_2CH_2CN$ |
| $H_5C_2OCH_2CH_2$ | $CH(CH_3)CH_2CN$ |
| $H_5C_2OCH_2CH_2$ | $CH_2CH(CH_3)CN$ |
| $H_5C_2OCH_2CH_2$ | $CH_2C\equiv CH$ |
| $H_5C_2SCH_2CH_2$ | $CH_3$ |
| $H_5C_2SCH_2CH_2$ | $C_2H_5$ |
| $H_5C_2SCH_2CH_2$ | $CH(CH_3)_2$ |
| $H_5C_2SCH_2CH_2$ | $CH_2CH=CH_2$ |
| $H_5C_2SCH_2CH_2$ | $CH_2CH_2CN$ |
| $H_5C_2SCH_2CH_2$ | $CH_2CH_2CH_2CN$ |
| $H_5C_2SCH_2CH_2$ | $CH(CH_3)CH_2CN$ |
| $H_5C_2SCH_2CH_2$ | $CH_2CH(CH_3)CN$ |
| $H_5C_2SCH_2CH_2$ | $CH_2C\equiv CH$ |
| $H_3COCH_2CH_2$ | $CH_3$ |
| $H_3COCH_2CH_2$ | $C_2H_5$ |
| $H_3COCH_2CH_2$ | $CH(CH_3)_2$ |
| $H_3COCH_2CH_2$ | $CH_2CH=CH_2$ |
| $H_3COCH_2CH_2$ | $CH_2CH_2CN$ |
| $H_3COCH_2CH_2$ | $CH_2CH_2CH_2CN$ |
| $H_3COCH_2CH_2$ | $CH(CH_3)CH_2CN$ |
| $H_3COCH_2CH_2$ | $CH_2CH(CH_3)CN$ |
| $H_3COCH_2CH_2$ | $CH_2C\equiv CH$ |
| $H_3CSCH_2CH_2$ | $CH_3$ |
| $H_3CSCH_2CH_2$ | $C_2H_5$ |
| $H_3CSCH_2CH_2$ | $CH(CH_3)_2$ |
| $H_3CSCH_2CH_2$ | $CH_2CH=CH_2$ |
| $H_3CSCH_2CH_2$ | $CH_2CH_2CN$ |
| $H_3CSCH_2CH_2$ | $CH_2CH_2CH_2CN$ |
| $H_3CSCH_2CH_2$ | $CH(CH_3)CH_2CN$ |
| $H_3CSCH_2CH_2$ | $CH_2CH(CH_3)CN$ |
| $H_3CSCH_2CH_2$ | $CH_2C\equiv CH$ |
| $H_3COCH_2CH_2CH_2$ | $CH_3$ |
| $H_3COCH_2CH_2CH_2$ | $C_2H_5$ |
| $H_3COCH_2CH_2CH_2$ | $CH(CH_3)_2$ |
| $H_3COCH_2CH_2CH_2$ | $CH_2CH=CH_2$ |
| $H_3COCH_2CH_2CH_2$ | $CH_2CH_2CN$ |
| $H_3COCH_2CH_2CH_2$ | $CH_2CH_2CH_2CN$ |
| $H_3COCH_2CH_2CH_2$ | $CH(CH_3)CH_2CN$ |
| $H_3COCH_2CH_2CH_2$ | $CH_2CH(CH_3)CN$ |
| $H_3COCH_2CH_2CH_2$ | $CH_2C\equiv CH$ |
| $H_3CSCH_2CH_2CH_2$ | $CH_3$ |
| $H_3CSCH_2CH_2CH_2$ | $C_2H_5$ |
| $H_3CSCH_2CH_2CH_2$ | $CH(CH_3)_2$ |
| $H_3CSCH_2CH_2CH_2$ | $CH_2CH=CH_2$ |
| $H_3CSCH_2CH_2CH_2$ | $CH_2CH_2CN$ |
| $H_3CSCH_2CH_2CH_2$ | $CH_2CH_2CH_2CN$ |
| $H_3CSCH_2CH_2CH_2$ | $CH(CH_3)CH_2CN$ |
| $H_3CSCH_2CH_2CH_2$ | $CH_2CH(CH_3)CN$ |
| $H_3CSCH_2CH_2CH_2$ | $CH_2C\equiv CH$ |
| $CH_2-CH_2-O-CH_2-CH_2$ | |
| $CH_2-CH_2-CH_2-CH_2$ | |
| $CH_2-CH=CH-CH_2$ | |
| $CH=CH-CH_2-CH_2$ | |
| $CH_2-CH_2-CH_2-CH_2-CH_2$ | |
| $CH_2-CH_2-O-CH(CH_3)-CH_2$ | |
| $CH_2-CH_2-O-CH_2-CH(CH_3)$ | |

TABLE 1-continued

| R$^1$ | R$^2$ |
|---|---|
| | CH$_2$—CH$_2$—N(CH$_3$)—CH$_2$—CH$_2$ |
| | CH$_2$—CH(CH$_3$)—O—CH(CH$_3$)—CH$_2$ |
| | CH$_2$—CH=CH—CH$_2$—CH$_2$ |
| | CH=CH—CH$_2$—CH$_2$—CH$_2$ |
| | CH$_2$—CH$_2$—CH$_2$—CH$_2$—CH(CH$_3$) |
| | CH$_2$—CH$_2$—CH$_2$—CH(CH$_3$)—CH$_2$ |
| | CH$_2$—CH$_2$—CH(CH$_3$)—CH$_2$—CH$_2$ |
| | CH$_2$—CH$_2$—CH$_2$—CH$_2$—CH(CH$_2$CH$_2$Cl) |
| | CH$_2$—CH$_2$—CH$_2$—CH(CH$_2$CH$_2$Cl)—CH$_2$ |
| | CH$_2$—CH$_2$—CH(CH$_2$CH$_2$Cl)—CH$_2$—CH$_2$ |

With regard to the tertiary amines A2, there are in principle no restrictions. Suitable amines A2 include trialkylamines, preferably trialkylamines having C$_1$-C$_4$-alkyl groups, such as trimethylamine, triethylamine, dimethylethylamine, dimethyl-n-propylamine, tri-n-propylamine, triisopropylamine, tri-n-butylamine, dimethyl-n-butylamine, N,N-dialkyl-N-cycloalkylamines preferably having C$_1$-C$_4$-alkyl groups and C$_6$-C$_8$-cycloalkyl groups, e.g. N,N-dimethyl-N-cyclohexylamine, and also N,N-dialkylanilines preferably having C$_1$-C$_4$-alkyl groups, in particular N,N-dimethylaniline, N,N-diethylaniline, N-methyl-N-ethylaniline, heterocyclic tertiary amines such as N-alkylmorpholines, N-alkylimidazoles and N-alkylpiperidines, such as N-methylmorpholine, N-ethylmorpholine, N-methylpiperidine, N-ethylpiperidine, N-ethylimidazole and N-methylimidazole, and also tertiary amines having an sp$^2$ nitrogen atom, which are also referred to hereinbelow as tertiary amines of the pyridine type. In addition to pyridine itself, these also include α-, β- and γ-picoline, pyrimidine, pyridazine, 2,4-lutidine, 2,6-lutidine, quinoline, quinaldine and also N-alkylimidazoles such as N-methylimidazole and N-ethylimidazole. Preferred tertiary amines are those of the pyridine type, in particular pyridine and α-, β- and γ-picoline, more preferably α-picoline.

Apart from sulfur trioxide itself, useful sulfur trioxide sources also include chlorosulfonic acids and the adducts of sulfur trioxide with the abovementioned tertiary amines. Among the adducts of sulfur trioxide with tertiary amines, preference is given to the adducts with picoline, pyridine, triethylamine and N,N-dimethyl-N-cyclohexylamine. These adducts can be prepared by adding sulfur trioxide or chlorosulfonic acid to a solution of the tertiary amine in a suitable solvent, preferably the solvent of the reaction. The addition is preferably effected in the range from −20 to +50° C. and in particular in the range from −10 to +30° C.

Further useful sulfur trioxide sources include the adducts of sulfur trioxide with secondary amides such as dimethylformamide, diethylformamide, di-n-propylformamide, dimethylacetamide, diethylacetamide, N-methylacetanilide, N-methylpyrrolidone and N-ethylpyrrolidone, the adducts with tetraalkylurea compounds such as tetramethylurea, tetraethylurea, tetrabutylurea and dimethylpropyleneurea, and also the adducts with electron-rich ethers such as tetrahydrofuran or pyran, or the adducts with nitrites such as acetonitrile or propionitrile. These adducts are prepared in a similar manner to the adducts of sulfur trioxide with tertiary amines. In step i), preference is given to sulfur trioxide or a sulfur trioxide adduct with an amine of the pyridine type, more preferably a sulfur trioxide adduct with α-picoline.

According to the invention, at least equimolar amounts, preferably at least 1.1 mol and in particular at least 1.2 mol, of SO$_3$ or SO$_3$ adduct (calculated as SO$_3$) are used per mole of amine A1 in the reaction of the primary or secondary amine A1 in step i). Advantageously, not more than 2.5 mol and in particular not more than 2 mol of sulfur trioxide or sulfur trioxide adducts will be used per mole of amine A1.

The amount of tertiary amine A2 used in step i) is preferably at least 2 mol, and in particlar at least 2.5 mol, per mole of amine A1. Advantageously, the amount of tertiary amine A2 is not more than 6 mol and in particular not more than 5 mol per mole of amine A1. In the case that the SO$_3$ source used is the adduct of SO$_3$ with a tertiary amine, the amount of tertiary amine A2 introduced in this way is also taken into account in the molar ratios previously mentioned, i.e. the molar data previously specified relate in each case to the total amount of tertiary amine in step i).

Customarily, the reaction in step i) is effected at temperatures in the range from −20° C. to +100° C. and preferably in the range from −10 to +60° C. The procedure is generally that the sulfur trioxide or sulfur trioxide source is initially charged in a suitable solvent or diluent, and tertiary amine A2 is then added. The addition is generally effected in the range from −20 to +100° C., preferably in the range from −10 to +50° C. and in particular in the range from −10 to +20° C. This reaction is frequently exothermic and is generally maintained within the desired temperature range by suitable measures of internal and/or external cooling. When the SO$_3$ source used is an adduct of SO$_3$ with a tertiary amine, the addition of the amine to the SO$_3$ source is generally less exothermic. The amine A1 is then added to the resulting solution or suspension. The amine A1 may be added either undiluted or in dissolved or suspended form in a solvent or diluent suitable therefor. This results in the formation of the ammonium sulfamate shown in scheme 1. The amine A1 is preferably added at temperatures in the range from −10 to +60° C. The reaction mixture obtained is frequently allowed to continue to react for some time after the addition, for example in the range from +10 to +80° C. and in particular in the range from +20 to +60° C.

In another embodiment of the invention, step i) is carried out in such a way that the primary or secondary amine A1 and the tertiary amine A2 are initially charged in a suitable solvent or diluent, and SO$_3$ or the SO$_3$ source is added thereto. SO$_3$ or the SO$_3$ source is likewise added in a suitable solvent or diluent. For the reaction temperatures, the same applies as was said above. Preference is given to adding at temperatures in the range from −20 to +80° C. and in particular in the range from −10 to +60° C. After the addition, the reaction mixture is allowed to continue to react for some time. In this time, the reaction temperatures are generally from +10 to +80° C. and preferably from +20 to +60° C.

The time necessary for the reaction in step i) is generally at least 15 minutes and will preferably not exceed 10 hours and in particular 5 hours.

The rate at which the tertiary amine is added to the SO$_3$ or SO$_3$ source in the first embodiment is of minor importance for the result of the reaction, and the addition is generally effected in a manner which allows temperature control by cooling. Depending on the size of the batch, the duration of the addition of the amine A2 is in the range from a few minutes to 1 hour. The rate of the addition of the amine A1 to the reaction mixture obtained in this way is likewise of minor importance and is frequently in the range from a few minutes up to 1 hour. To complete the reaction, the reaction is generally allowed to continue for a few minutes to a few hours, for example from 5 min to 3 h. However, reaction times of more than one hour are frequently unnecessary. In principle, it is possible to isolate that ammonium sulfamate obtained in step i) and then to react it in step ii) with at least the amount of a phosphorus halide required by the stoichiometry. However, preference is given to carrying out the reaction in step ii) without previously isolating the ammonium sulfamate from the reaction mixture obtained in step i), i.e. the phosphorus halide is added directly to the reaction mixture obtained in step i).

Suitable phosphorus halides are the customary commercially obtainable phosphorus halides, in particular the chlorides and the bromides, and more preferably the chlorides. Examples of suitable phosphorus halides include phosphorus trichloride, phosphorus pentachloride, phosphorus oxychloride, phosphorus tribromide and phosphorus pentabromide. Preference is given to phosphorus trichloride, phosphorus pentachloride and in particular to phosphorus oxychloride(=phosphoryl chloride).

The phosphorus halide may be added either undiluted or in an inert solvent or diluent. In the case of liquid phosphorus halides such as phosphoryl chloride, it is generally unnecessary to dissolve or dilute.

The minimum amount of phosphorus halide required depends in a manner known per se on the stoichiometry of the reaction and, in the case of phosphorus pentachloride, is at least 0.5 mol per mole of amine A1 and, in the case of phosphorus trichloride, phosphorus tribromide and phosphorus oxychloride, at least 1 mol per mole of amine A1. Advantageously, the amount of phosphorus halide will not exceed 3 mol per mole of amine A1 and preferably 2.2 mol per mole of amine A1. When phosphorus trichloride, phosphorus tribromide or phosphorus oxychloride is used, the amount of phosphorus halide is preferably from 1 to 3 mol and in particular from 1.1 to 2.2 mol per mole of amine A1. When phosphorus pentachloride or phosphorus pentabromide is used, the amount is preferably from 0.5 to 1 mol, in particular from 0.6 to 0.9 mol, per mole of amine A1.

The reacton time required for step ii) is generally in the range from 0.5 to 8 hours.

The reaction temperatures required for step ii) are generally in the range from 0 to 100° C., preferably in the range from 10 to 80° C. and in particular in the range from 20 to 80° C.

Suitable solvents or diluents for steps i) and ii) are those which are inert under the reaction conditions, i.e. toward $SO_3$ and phosphorus halides. Such solvents are known to those skilled in the art and include both polar and nonpolar aprotic compounds such as cyclic or open-chain ethers, halohydrocarbons, nitrohydrocarbons, aromatic, aliphatic and cycloaliphatic hydrocarbons, tetraalkylureas, N-alkyllactams, N,N-dialkylamides and their mixtures. Examples of ethers include diethyl ether, di-n-propyl ether, methyl tert-butyl ether and ethylene glycol dimethyl ether. In addition to nitromethane, examples of nitrohydrocarbons include nitrobenzene, o-, m- or p-chloronitrobenzenes, and o-, p-nitrotoluenes. Examples of hydrocarbons include benzene, toluene, xylenes, hexane, heptane, octane and cyclohexane. An example of tetraalkylureas is tetramethylurea. Examples of N,N-dialkylamides include dimethylformamide and dimethylacetamide. An example of N-alkyllactams is N-methylpyrrolidone. Examples of halohydrocarbons include aliphatic halohydrocarbons such as methylene chloride, 1,1- and 1,2-dichloroethane, cis-1,2-dichloroethene, 1,1-, 1,2- and 1,3-dichloropropane, 1,4-dichlorobutane, tetrachloroethane, 1,1,1- and 1,1,2-trichloroethane, trichloroethylene, pentachloroethane, trichlorofluoromethane, chlorobenzene, dichlorobenzenes, chlorotoluenes, dichlorotoluenes, trichlorobenzene and their mixtures. Preferred solvents include halohydrocarbons, in particular dichloroethane, dichloromethane and chlorobenzene, and also their mixtures. Useful diluents are in principle also the aforementioned tertiary amines.

The amount of diluent is generally selected in such a way that the reaction mixtures remain flowable during the reaction, and the amount sufficient for this purpose is generally at least 500 ml, preferably at least 1 l, of solvent per mole of amine A1. These data relate to the total amount of solvent in reaction steps i) and ii). It will be appreciated that, for reasons of cost, the minimum amounts of solvent will be used. In general, the amount of solvent will therefore not be more than 5 l per mole of amine A1.

Process steps i) and ii) may be operated either batchwise or continuously in reaction vessels suitable therefor. In the batchwise method, stirred tanks and stirred reactors will customarily be used. These are generally equipped with suitable heat exchangers or a cooling jacket for removing the heat of reaction. The continuous performance of the reaction steps i) and ii) is likewise effected in the reactors customary therefor, for example in stirred tanks, stirred tank batteries and tubular reactors, although preference is given to reactors having low backmixing.

The reaction mixture obtained in step ii) is worked up in a manner known per se. Frequently, to decompose excess phosphorus halide, the reaction mixture obtained in step ii) will be hydrolyzed by pouring into water, and excess amine A1 or A2 will be extractively removed with a water-immiscible organic solvent after the addition of dilute acid, in particular dilute mineral acid. It is likewise possible to distill off excess phosphorus halide and solvent and also any excess tertiary amine A2 and then to fractionally distill the residue. It is also possible, after distillative removal of volatile constituents, to admix the residue obtained with an organic, moderately polar or nonpolar solvent in which salts of tertiary amines have limited solubility. Suitable solvents are open-chain ethers, in particular diethyl ether, diisopropyl ether and methyl tert-butyl ether. In this way, a solution of the sulfamoyl halide is obtained.

After evaporating the solvent, the sulfamoyl halide is generally obtained in sufficient purity to allow its direct use in the preparation of crop protection agents, without requiring further purification stages. The purities achieved without distillation are frequently around 90% and in particular around 95% and above. For this reason, the process according to the invention may advantageously dispense with a distillation. However, it will be appreciated that a distillation is possible in principle.

The process according to the invention delivers the sulfamoyl halides in very good yields of generally at least 80% and frequently at least 90%, based on the amine A1.

In addition, the process according to the invention does not entail the detour via carbamic acids or isocyanates and also circumvents the problematic use of chlorine and the preparation of chloroamines.

The process according to the invention makes it possible in principle to prepare any desired sulfamoyl halides-which are derived from primary or secondary amines. It is also possible to use those amines which have comparatively reactive functionalities, in particular C=C double bonds, C≡C triple bonds, aldehyde or keto carbonyl groups, ether groups, ester groups, amide groups and the like. Such sulfamoyl halides are novel and likewise form part of the subject-matter of the present invention. In particular, the present invention relates to sulfamoyl halides of the formula II $$Cl—SO_2—NR^{1'}R^{2'} \qquad (II),$$

where
$R^{1'}$ is $C_2$-$C_{20}$-alkenyl, $C_2$-$C_{20}$-alkynyl, $C_2$-$C_{20}$-haloalkenyl, $C_2$-$C_{20}$-haloalkynyl, $C_2$-$C_{20}$-alkyl which is substituted by CN, $C_1$-$C_4$-alkoxy, $C_2$-$C_{20}$-haloalkenyl, $C_2$-$C_{20}$-haloalkynyl, $C_5$-$C_{10}$-cycloalkenyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or formyl, or is $C_5$-$C_{10}$-cycloalkenyl, and $R^{2'}$ is $C_2$-$C_{20}$-alkyl, $C_2$-$C_{20}$-alkenyl or $C_2$-$C_{20}$-alkynyl, each of which may be unsubstituted or substituted by CN, $NO_2$, $C_1$-$C_4$-alkoxy, $C_1$-$C_4$-alkylthio, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, phenyl which may itself have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro or cyano, or is
$C_1$-$C_{20}$-haloalkyl, $C_2$-$C_{20}$-haloalkenyl, $C_2$-$C_{20}$-haloalkynyl, $C_3$-$C_{10}$-cycloalkyl, $C_5$-$C_{10}$-cycloalkenyl, heterocyclyl having from one to 3 heteroatoms selected from O, S and N, phenyl or naphthyl, where heterocyclyl, phenyl or naphthyl may themselves have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro or cyano, and is especially $C_1$-$C_4$-alkyl, allyl, propargyl or phenyl which is unsubstituted or substituted by halogen, methoxy or methyl;

$R^{1'}$ and $R^{2'}$ together may also form a partially unsaturated 5- to 8-membered nitrogen heterocycle which may itself be substituted by $C_1$-$C_4$-alkyl, $C_1$-$C_4$-alkoxy and/or $C_1$-$C_4$-haloalkyl, and have one or 2 carbonyl groups or thiocarbonyl groups and/or one or two further heteroatoms selected from O, S and N as ring members, where $R^{2'}$ may also be methyl when $R^{1'}$ is $C_2$-$C_{20}$-alkynyl, $C_2$-$C_{20}$-haloalkenyl, $C_2$-$C_{20}$-alkyl which is substituted by $C_2$-$C_{20}$-haloalkenyl, $C_2$-$C_{20}$-haloalkynyl, $C_5$-$C_{10}$-cycloalkenyl or formyl, or is $C_5$-$C_{10}$-cycloalkenyl, excluding compounds of the general formula II where $R^{1'}$ and $R^{2'}$ are each allyl.

A preferred embodiment of the invention relates to sulfamoyl chlorides of the general formula II where $R^{1'}$ and $R^{2'}$ are each independently, and preferably in combination, defined as follows:
$R^{1'}$ in particular $C_1$-$C_4$-alkoxy-$C_2$-$C_4$-alkyl, cyano-$C_2$-$C_4$-alkyl, $C_3$-$C_{10}$-alkenyl, $C_3$-$C_{10}$-alkynyl or $C_3$-$C_{10}$-haloalkenyl, and especially 2-methoxyethyl, 2-cyanoethyl, allyl, propargyl or 2-chloroallyl;
$R^{2'}$ $C_2$-$C_4$-alkyl, allyl, propargyl or phenyl which is unsubstituted or substituted by halogen, methoxy or methyl, or
$R^{1'}$ and $R^{2'}$ together with the nitrogen atom to which they are bonded are 2,5-dihydropyrrol-1-yl, 2,3-dihydropyrrol-1-yl or 1,2,3,4- or 1,2,3,6-tetrahydropyridin-1-yl, where the heterocycles may have 1, 2 or 3 methyl groups.

A further embodiment of the invention relates to sulfamoyl chlorides of the general formula II where
$R^{1'}$ is phenyl or naphthyl, each of which may have 1, 2, 3 or 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro or cyano, and
$R^{2'}$ is $C_1$-$C_{10}$-alkyl or $C_3$-$C_{10}$-cycloalkyl.

The sulfamoyl halides obtained by the process according to the invention may be converted to the corresponding sulfamoyl amides(=sulfuric diamides) in analogy to existing methods by reaction with ammonia. The reaction affords the compounds in high yields. Such sulfamoyl amides have hitherto been prepared by reaction of by partially hydrolyzing chlorosulfonyl isocyanate to chlorosulfonamide Cl—$SO_2$—$NH_2$ and subsequently reacting the chlorosulfonamide with a primary or secondary amine (see, for example, WO 00/83459). However, the sulfamoyl amides are obtainable by this route only in moderate yields of generally <50%. In addition, the process entails the use of the highly reactive, very moisture-sensitive and expensive chlorosulfonyl isocyanate.

According to the invention, the sulfuric diamides are prepared by:
i) reacting a primary or secondary amine A1 with at least equimolar amounts of $SO_3$ or an $SO_3$ source in the presence of at least equimolar amounts of a tertiary amine A2, based in each case on the amine A1, and
ii) reacting the reaction mixture obtained in step i) with at least the amount of a phosphorus halide required by the stoichiometry and
iii) reacting the sulfamoyl halide obtained in step ii) with ammonia.

The process according to the invention for preparing the sulfuric diamides affords the appropriate sulfuric diamides in very high yields and therefore likewise forms part of the subject matter of the present invention. The use of chlorosulfonyl isocyanate in this process is unnecessary.

The sulfuric diamides obtainable by this route, in particular those of the general formula III

$$NH_2-SO_2-NR^1R_2 \qquad (III)$$

where $R^1$ and $R^2$ are as defined above, are suitable for preparing compounds of the general formula IV

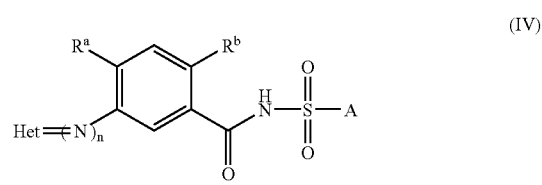

(IV)

as described in WO 01/83459. In formula IV, n is 0 or 1, Het is an optionally substituted 5- or 6-membered heterocycle which may have 1, 2 or 3 nitrogen atoms, optionally one further heteroatom selected from oxygen and sulfur, and optionally one or two carbonyl or thiocarbonyl groups as ring members. $R^a$ is hydrogen, fluorine or chlorine, $R^b$ is chlorine or cyano, and A is a radical derived from a primary or secondary amine A1, in particular is $NHR^3$ or $NR^1R^2$ where $R^1$ and $R^2$ are each as previously defined and $R^3$ has the same definition as $R^1$.

The present invention therefore also relates to a process for preparing compounds of the general formula II. This process comprises the following steps:
i) reacting a primary or secondary amine A1 with at least equimolar amounts of $SO_3$ or an $SO_3$ source in the presence of at least equimolar amounts of a tertiary amine A2, based in each case on the amine A1, to obtain an ammonium sulfamate;
ii) reacting the ammonium sulfamate with at least the amount of a phosphorus halide required by the stoichiometry, to obtain a sulfamoyl halide of the amine A1;
iii) reacting the sulfamoyl halide obtained in step ii) with ammonia to obtain a sulfamoyl amide; and iv) reacting the reaction product from step iii) with a compound of the general formula V

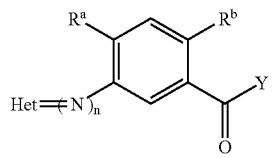

where Het, n, $R^a$ and $R^b$ are each as defined for formula IV and Y is OH, alkoxy or a halogen atom.

Examples of suitable heterocycles are the radicals of the formulae Q1 to Q40 disclosed in WO 01/83459, which are incorporated herein by way of reference. Het(=N)$_n$— preferably represents radicals of the formulae Q5, Q7, Q12, Q13, Q21, Q22, Q27, Q32, Q36, Q38, Q39, and Q40 disclosed in WO 01/83459, for example optionally substituted pyrimidine-2,6-dion-1-yl such as 4-trifluoromethylpyrimidine-2,6-dion-1-yl, 3-methyl-4-trifluoromethylpyrimidine-2,6-dion-1-yl or 3-amino-4-trifluoromethylpyrimidine-2,6-dion-1-yl, optionally substituted 1,2,4-triazol-5-on-1-yl such as 3-methyl-4-difluoromethyl-1,2,4-triazol-5-on-1-yl, optionally substituted 1,3,5-triazine-4,6-dion-5-yl such as 1,3-dimethyl-2-thio-1,3,5-triazine-4,6-dion-5-yl or 3,5-dimethyl-1,3,5-triazine-2,4,6-trion-1-yl, optionally substituted 1,2,4-triazin-6-yl such 2,4-dimethyl-3-thio-1,2,4-triazin-5-on-6-yl, optionally substituted pyrazin-3-on-2-yl such as 5-trifluoromethylpyrazin-3-on-2-yl, 4-methyl-5-trifluoromethylpyrazin-3-on-2-yl or 4-amino-5-methylsulfonylpyrazin-3-on-2-yl, optionally substituted pyrazole such as 4-chloro-1-methyl-5-difluoromethoxypyrazol-3-yl, 4-bromo-1-methyl-5-difluoromethoxypyrazol-3-yl, 4-chloro-1-methyl-5-trifluoromethylpyrazol-3-yl or 4-bromo-1-methyl-5-trifluoromethylpyrazol-3-yl, optionally substituted pyridinyl such as 3-chloro-5-trifluoromethylpyridin-2-yl, 3,4,5,6-tetrahydrophthalimidyl, a radical of the formula:

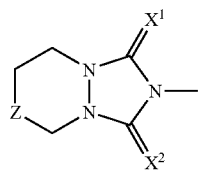

where $X^1$, $X^2$ and Z are each independently oxygen or sulfur, and in particular a radical of the general formula

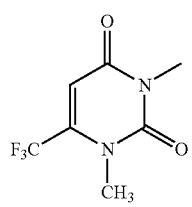

when n=0.

With regard to steps i) and ii), the same applies as was said above. Step iii) is generally carried out by reacting the sulfamoyl halide, preferably the chloride, with $NH_3$ or an aqueous ammonia solution in a suitable solvent or diluent. In addition to the abovementioned solvents, suitable solvents or diluents are in particular water and water-miscible solvents and diluents. Preference is given to effecting the reaction in aqueous ammonia, in particular in from 5 to 35% by weight aqueous ammonia.

Preferably, the procedure is to add the sulfamoyl halide, optionally diluted in an inert solvent, to the solution of the $NH_3$ in a solvent, preferably to an aqueous ammonia solution. It will be appreciated that the sulfamoyl halide may also be initially charged, preferably in a solvent or diluent, and gaseous $NH_3$ or a solution of $NH_3$ in a solvent, in particular aqueous ammonia, may be added thereto. Preference is given to using $NH_3$ in excess, based on the stoichiometry of the reaction. In particular, at least 2.5 mol of $NH_3$, e.g. from 2.5 to 50 mol of $NH_3$, in particular from 3 to 20 mol of $NH_3$, will be used per mole of sulfamoyl halide.

The temperatures required for the reaction are generally in the range from –20 to 100° C. and preferably in the range from –10 to 30° C. The reaction time is generally in the range from 10 min to 5 h and preferably in the range from 0.5 h to 3 h. The sulfamoyl amide obtained in the reaction is worked up in a manner known per se, for example by removing the solvents and separating from the salts formed in the reaction.

The step iv) in turn is effected in a manner known per se, for example as described in WO 01/83459, pp. 31-35, by reacting the compound of the formula V with the amounts required by the stoichiometry of the sulfamoyl amide obtained in stage iii) from the corresponding sulfamoyl chloride.

When Y is OH, the reaction is effected, for example, in the presence of dehydrating agents such as N,N'-carbonyldiimidazole or dicyclohexylcarbodiimide in an inert organic solvent, and the reaction is optionally carried out in the presence of a tertiary amine or an amidine base such as DBU (1,8-diazabicyclo-[5.4.0]undec-7-ene or DBN (1,5-diazabicyclo[4.3.0]non-5-ene) to accelerate the reaction. Alternatively, compounds V where Y=OH may also initially be converted into their acid halides and then reacted with the sulfamoyl amide. Such reactions are known to those skilled in the art, for example from Houben Weyl, Methoden der Organischen Chemie, Vol. E5 (1985), section I, p. 587 ff. and Vol. E5 (1985), section II, p. 934 ff. For further details, reference is also made at this point to WO 01/83459.

The examples which follow are intended to illustrate the invention without restricting it.

I. Preparation of Sulfamoyl Halides

EXAMPLE 1

N-(2-Chloro-2-propen-1-yl)-N-(n-propyl)sulfamoyl chloride 35.7 g (0.256 mol) of sulfur trioxide as a 57.4% solution in 1,2-dichloroethane were added with stirring at from 0 to 5° C. within 15 min to a solution of 43.7 g (0.469 mol) of α-picoline in 200 ml of 1,2-dichloroethane, followed by washing with 40 ml of 1,2-dichloroethane and stirring for 15 min-until the temperature rose to 20° C. 28.5 g (0.192 mol) of 90% pure N-(2-chloro-2-propen-1-yl)-N-propylamine were then added within 15 min with stirring and external cooling at from 20 to 30° C., followed by washing with 40 ml of 1,2-dichloroethane and stirring at 50° C. for 15 min. After cooling to 23° C., 39.3 g (0.256 mol) of phosphorus oxychloride were added with stirring within 15 min, followed by washing with 120 ml of 1,2-dichloroethane and heating to 70° C. After stirring for 1 h, the reaction mixture was cooled and concentrated under reduced pressure, and the residue obtained was stirred with 100 ml of methyl tert-butyl ether each time. The methyl tert-butyl ether phases were decanted off and concentrated. The residue was distilled. 42.5 g (90.5% of theory) of the title compound having a boiling point of 67-71° C./0.4 mbar were obtained.

EXAMPLE 2

N-Methyl-N-[1-methylethyl]sulfamoyl chloride 63.2 g (0.41 mol) of sulfur trioxide as a 52% solution in 1,2-dichloroethane were added with stirring at from 0 to 5° C. within 15 min to a solution of 70.0 g (0.752 mol) of α-picoline in 250 ml of 1,2-dichloroethane, followed by washing with 50 ml of 1,2-dichloroethane and stirring for 15 min until the temperature rose to 25° C. 26.3 g (0.342 mol) of 95% pure N-methyl-N-[1-methylethyl]amine were then added within 15 min with stirring at from 20 to 35° C., followed by washing with 50 ml of 1,2-dichloroethane and stirring at 55° C. for 15 min. After cooling to 20° C., 42.7 g (0.205 mol) of phosphorus pentachloride were added with stirring at from 20 to 32° C. within 15 min with external cooling, followed by washing with 150 ml of 1,2-dichloroethane. After stirring at 70° C. for 2 h, the reaction mixture was concentrated under reduced pressure and distilled via a Normag column head having a 10 cm column. 35 g (59.6% of theory) of the title compound having a boiling point of 110-115° C./30 mbar were obtained. Refractive index $n_D^{23}$=1.4620.

EXAMPLE 3

N-Isopropyl-N-(n-propyl)sulfamoyl chloride 52.6 g (0.356 mol) of sulfur trioxide as a 60% solution in 1,2-dichloroethane were added with stirring at from 0 to 5° C. within 25 min to a solution of 60.75 g (0.652 mol) of α-picoline in 400 ml of 1,2-dichloroethane, followed by washing with 80 ml of 1,2-dichloroethane and stirring for 15 min until the temperature rose to 22° C. 30 g (0.296 mol). of N-isopropyl-N-(n-propyl)amine were then added within 20 min with stirring and external cooling at from 20 to 30° C., followed by washing with 80 ml of 1,2-dichloroethane and stirring at 50° C. for 15 min. After cooling to 25° C., 54.6 g (0.356 mol) of phosphorus oxychloride were added with stirring and cooling to 25-30° C. within 15 min, followed by washing with 200 ml of 1,2-dichloroethane and heating to 75° C. After stirring at this temperature for 1 h, the reaction mixture was cooled and concentrated under reduced pressure, and the residue obtained was stirred 3 times with 200 ml each time of methyl tert-butyl ether. The methyl tert-butyl ether phases were decanted off and extracted twice with dilute hydrochloric acid. The organic phase was dried over magnesium sulfate, the drying agent was filtered off and the organic phase was concentrated. 55.1 g (91.3% of theory) of the title compound having a refractive index $n_D^{23}$=1.4605 were obtained. A gas chromatography analysis (column: Macherey and Nagel 25 m Optima 17 GC 9; pressure 14.5 psi; helium; column flow 0.6 ml/min; split, 30 ml/min; injector 280° C., detector 320° C.) showed a degree of purity of 96% (RT=11.87 min).

EXAMPLE 13

N-Allyl-N-(2-cyanoethyl)sulfamoyl chloride 64.8 g (0.641 mol) of sulfur trioxide were added as a 57% solution in 1,2-dichloroethane at from 0 to 5° C. with stirring within 15 minutes to a solution of 90.6 g (0.846 mol) of 2,6-lutidine in 200 ml of 1,2-dichloroethane, followed by washing with 40 ml of 1,2-dichloroethane and stirring for 15 minutes until the temperature had risen to 22° C. Subsequently, 42.4 g (0.385 mol) of N-allyl-N-(2-cyanoethyl)amine were added at from 20 to 30° C. with stirring within 15 minutes, followed by washing with 40 ml of 1,2-dichloroethane and stirring at 50° C. for 15 minutes. After cooling to 22° C., 70.8 g (0.61 mol) of phosphorus oxychloride were added with stirring at from 20 to 30° C. within 15 minutes, followed by washing with 120 ml of 1,2-dichloroethane and heating to 70° C. After stirring at this temperature for 1 hour, the reaction mixture was allowed to cool to 25° C., concentrated under reduced pressure and distilled through a Normag column head with a 10 cm column. 32.3 g (40% of theory) of the title compound with a b.p. of from 110 to 116° C./0.4 mbar were obtained. Refractive index: $n_D^{23}$=1.4948.

The sulfamoyl chlorides $R^1R^2N$—$SO_2$—Cl, described in Table 2, of Examples 4 to 24 were prepared in a similar manner to Example 1. In Table 2, boiling point [b.p. in ° C.], the refractive index [$n_D^{23}$ or $n_D^{25}$], the GC retention time RT (in min) in the case of GC analysis (see below) and the degree of purity, and also the yield are reported.

TABLE 2

| Ex. | $R^1$ | $R^2$ | b.p. [° C.]/mbar or RT [min]; purity[1] | $n_D^{23}$ (* = $n_d^{25}$) | Yield [%] |
| --- | --- | --- | --- | --- | --- |
| 4 | $C_2H_5$ | n-C3H7 | 45–46/0.3 | 1.4599 | 89 |
| 5 | $C_2H_5$ | i-C3H7 | 49–52/0.3 | 1.4627 | 72.5 |
| 6 | $CH_2$—CH=CH—$CH_2$—$CH_2$ | | 58–60/0.4 | 1.5102* | 88.5 |
| 7 | $CH_2$—CH($CH_3$)—$CH_2$—$CH_2$—$CH_2$ | | 67–72/0.3 | 1.4908 | 78.8 |
| 8 | $CH_2$—CH($CH_3$)—O—$CH_2$—$CH_2$ | | 61–64/0.2 | 1.4932 | 74.6 |
| 9 | CH($CH_2$CH2Cl)—$CH_2$—$CH_2$—$CH_2$—$CH_2$ | | 120–122/0.3 | 1.5172 | 75 |
| 10 | n-$C_3H_7$ | $CH_3O(CH_2)_2$ | 63–70/0.4 | 1.4619* | 85.5 |
| 11 | n-$C_3H_7$ | $CH_2$=CH—$CH_2$— | 11.52; 96% | 1.4695 | 79.4 |
| 12 | c-$C_6H_{11}$ | $CH_2$=CH—$CH_2$— | | | |
| 13 | NC$(CH_2)_2$ | $CH_2$=CH—$CH_2$ | b.p. 110–116/0.4 | 1.4948 | 40[2] |

TABLE 2-continued

| Ex. | R¹ | R² | b.p. [° C.]/mbar or RT [min]; purity[1] | $n_D^{23}$ (* = $n_d^{25}$) | Yield [%] |
|---|---|---|---|---|---|
| 14 | NC(CH₂)₂ | EtS(CE₂)₂ | | | |
| 15 | NC(CH₂)₂ | C₂H₅ | | | |
| 16 | NC(CH₂)₂ | i-C₃H₇ | | | |
| 17 | NC(CH₂)₂ | CH₃O(CH₂)₃ | | | |
| 18 | 4-Cl-C₆H₄ | CH₃ | | | |
| 19 | 4-Br-C₆H₄ | i-C₃H₇ | f.p. 93–95 | | 55.5 |
| 20 | 3-Cl-C₆H₄ | CH₃ | | | |
| 21 | 2-Cl-C₆H₄ | CH₃ | | | |
| 22 | CH₃ | CH₂=CH—CH₂ | | | |
| 23 | CH₃ | (CH₃)₃C | | | |
| 24 | CH₃ | HC≡C—CH₂ | 9.53; 95% | 1.4783 | 69.2 |
| 25 | CH₂CH₃ | CH₂=CH—CH₂ | | | |
| 26 | CH₂CH₂CH₂Cl | CH₂=CH—CH₂ | | | |
| 27 | CH(CH₃)₂ | CH₂=CH—CH₂ | 12.19 96.4% | 1.4735 | 96 |
| 28 | CH₂CH₂CH₂CH₃ | CH₂=CH—CH₂ | | | |
| 29 | CH(CH₃)CH₂CH₃ | CH₂=CH—CH₂ | | | |
| 30 | CH₂CH₃ | HC≡C—CH₂ | | | |
| 31 | CH(CH₃)₂ | HC≡C—CH₂ | 12.27; 97.8% | 1.4780 | 78.3 |
| 32 | CH₂CH₂CH₂CH₃ | HC≡C—CH₂ | | | |
| 33 | CH₂CH(CH₃)₂ | HC≡C—CH₂ | | | |
| 34 | CH(CH₃)CH₂CH₃ | HC≡C—CH₂ | | | |
| 35 | CH₃ | CH2CH(CH3)2 | | | |
| 36 | CH(CH₃)₂ | CH₂CH₃ | | | |
| 37 | CH(CH₃)₂ | CH₂CH₂CH₂CH₃ | | | |
| 38 | CH(CH₃)₂ | CH₂CH(CH₃)₂ | | | |
| 39 | CH(CH₃)₂ | CH(CH₃)CH₂CH₃ | | | |
| 40 | CH₂—CH=CH—CH₂ | | | | |
| 41 | CH₂—CH(CH₃)—O—CH(CH₃)—CH₂ | | | | |
| 42 | CH₂—CH₂—CH₂—CH₂—CH₂ | | 14.72; 98.3% | 1.4935 | 90.9 |
| 43 | CH₂—CH₂—CH(CH₃)—CH₂—CH₂ | | 15.32; 98.3% | 1.4860 | 94.0 |
| 44 | CH₂CH₂CH₃ | HC≡C—CH₂ | | | |
| 45 | Phenyl | CH₃ | 17.75; 94.8% | 1.5442 | 71.8 |
| 46 | Phenyl | CH₂CH₃ | | | |
| 47 | Cyclohexyl | CH₃ | 17.98; 94.8% | 1.4960 | 90.8 |
| 48 | Cyclohexyl | CH₂CH₃ | 18.59; 98.6% | 1.4938 | 63 |

[1](column: Macherey and Nagel 25 m Optima 17 GC 9; pressure 14.5 psi; helium; column flow 0.6 ml/min; split 30 ml/min; injector 280° C., detector 320° C.)
[2]High-loss distillation II. Preparation of Sulfamoyl Amides

EXAMPLE 49

N-Methyl-N-isopropylsulfamoyl amide 15 g (0.083 mol) of N-methyl-N-isopropylsulfamoyl chloride from Example 2 were added with stirring at from 0 to 5° C. within 5 min to 49 ml (0.654 mol) of 25% aqueous ammonia and stirred at from 5 to 10° C. for a further 45 min. After concentrating the reaction mixture under reduced pressure, the residue was stirred in methylene chloride, removed from the insoluble sediment, washed and concentrated again under reduced pressure. 11.3 g of the title compound of m.p. 51-53° C. were obtained. Based on the purity determined in the NMR spectrum of 95%, the yield was 84.9% of theory.

In a similar manner, the sulfamoyl amides specified in Table 3 of the formula III $$NH_2—SO_2—NR^1R^2 \quad (III)$$

were prepared (Examples 50 to 63):

TABLE 3

| Example | R$^1$ | R$^2$ | f.p. [° C.] or n$_D^{23}$ | Yield [%] |
|---|---|---|---|---|
| 50 | CH$_2$CH$_2$CH$_3$ | CH(CH$_3$)$_2$ | 74–76 | 75.8 |
| 51 | HC≡C—CH$_2$ | CH(CH$_3$)$_2$ | 1.4850 | 71.6 |
| 52 | CH$_2$=CH—CH$_2$ | CH$_2$CH$_2$CH$_3$ | 36–38 | 78.4 |
| 53 | CH$_2$—CH$_2$—CH$_2$—CH$_2$—CH$_2$ | | 118–120 | 72.0 |
| 54 | CH$_2$—CH$_2$—CH(CH$_3$)—CH$_2$—CH$_2$ | | 126–129 | 68.2 |
| 55 | Cyclohexyl | CH$_3$ | 117–119 | 77.0 |
| 56 | CH$_3$CH$_2$CH$_2$ | CH$_3$OCH$_2$CH$_2$ | 1,4694 | 96 |
| 57 | CH$_2$—CH$_2$—CH=CH—CH$_2$ | | 116–118 | 33 |
| 58 | CH$_2$=C(Cl)CH$_2$ | CH$_2$CH$_2$CH$_3$ | 40–41 | 33 |
| 59 | CH$_2$CH(CH$_3$)CH$_2$CH$_2$CH$_2$ | | 62–64 | 81 |
| 60 | C$_2$H$_5$ | CH(CH$_3$)$_2$ | 49–51 | 89 |
| 61 | NC—CH$_2$CH$_2$ | CH$_2$CH=CH$_2$ | 75–77 | 44 |
| 62 | C$_6$H$_5$ | CH$_3$ | 73–76 | 61 |
| 63 | CH(CH$_3$)$_2$ | CH$_2$CH=CH$_2$ | 48–50 | 77 |

EXAMPLE 64

3-(5-(N-Methyl-N-phenyl)sulfamoylcarboxamide-4-chloro-2-fluorophenyl)-1,2,3,4-tetrahydro-1-methyl-6-trifluoromethylpyrimidine-2,4-dione 1.2 g (3.116 mmol) of 2-chloro-4-fluoro-5-(3-methyl-2,6-dioxo-4-trifluoromethyl-3,6-dihydro-2H-pyrimidin-1-yl)benzoyl chloride were added at 0° C. to a mixture of 0.64 g (3.428 mmol) of N-methyl-N-phenylsulfuric diamide, 0.69 g (6.885 mmol) of triethylamine and a spatula-tip of p-dimethylaminopyridine as a catalyst in 40 ml of methylene chloride. The mixture was stirred at 22° C. for 1 hour and the reaction solution was then extracted with 1N hydrochloric acid. After the organic phase had been dried over magnesium sulfate, the organic phase was concentrated under reduced pressure. The resulting residue was stirred with ether to obtain 1.3 g (78% of theory) of the title compound with an m.p. of 188-192° C.

The preparation was effected in analogy to the process A specified on p. 31 of WO 01/83459.

Analogously to example 64, the compounds specified in table 4 of the formula

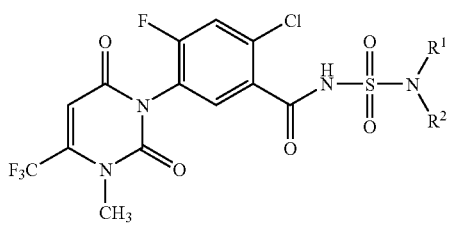

were prepared (examples 65 to 71).

TABLE 4

| Compound | R$^1$ | R$^2$ | m.p. [° C.] | Yield [%] |
|---|---|---|---|---|
| 65 | CH$_2$CH=CH$_2$ | CH$_2$CH$_2$CH$_3$ | 156–158 | 78 |
| 66 | CH$_2$CH=CH$_2$ | CH(CH$_3$)$_2$ | 138–140 | 66 |
| 67 | CH$_2$—CH$_2$—CH$_2$—CH$_2$ | | 211–213 | 80 |
| 68 | CH$_3$ | Cyclohexyl | 134–137 | 83 |
| 69 | CH$_3$ | CH(CH$_3$)$_2$ | 91–95 | 45 |
| 70 | CH$_2$CH=CH$_2$ | (CH$_2$)$_2$CN | 97 | 69 |
| 71 | CH$_2$CH$_2$CH$_3$ | (CH$_2$)$_2$OCH$_3$ | 124–126 | 81 |

The invention claimed is:

1. A process for preparing sulfamoyl halides of primary or secondary amines, comprising the following steps:
   i) reacting a primary or secondary amine A1 with at least equimolar amounts of SO$_3$ or an SO$_3$ source in the presence of at least equimolar amounts of a tertiary amine A2, based in each case on the amine A1, and
   ii) reacting the reaction mixture obtained in step i) with at least the amount of a phosphorus halide required by the stoichiometry.

2. A process as claimed in claim 1, wherein at least 2 mol of tertiary amine A2 are used per mole of amine A1.

3. A process as claimed in claim 1, wherein 1.1 mol of SO$_3$ or SO$_3$ source are used per mole of amine A1.

4. A process as claimed in claim 1, wherein the SO$_3$ source used in step i) is SO$_3$ or an adduct of a tertiary amine A2 with SO$_3$.

5. A process as claimed in claim 1, wherein the tertiary amine is a pyridine compound.

6. A process as claimed in claim 1, wherein the phosphorus halide is selected from phosphorus trichloride and phosphorus oxychloride.

7. A process as claimed in claim 6, wherein the amount of phosphorus halide is from 1 to 3 mol per mole of amine A1.

8. A process as claimed in claim 1, where the phosphorus chloride is selected from phosphorus pentachloride.

9. A process as claimed in claim 8, wherein the amount of phosphorus compound is from 0.5 to 1 mol per mole of amine A2.

10. A process as claimed in claim 1, wherein step ii) is carried out without isolating the ammonium sulfamate by adding the phosphorus halide to the reaction mixture obtained in step i).

11. A process as claimed in claim 1, wherein the secondary amine has the following formula IB:

$$H—NR^1R^2 \quad (IB)$$

where
R$^1$ and R$^2$ are each independently C$_1$-C$_{20}$-alkyl, C$_2$-C$_{20}$-alkenyl or C$_2$-C$_{20}$-alkynyl,
  each of which may be unsubstituted or substituted by C$_1$-C$_4$-alkoxy, C$_1$-C$_4$-alkylthio, CN, NO$_2$, formyl, C$_1$-C$_4$-alkylcarbonyl, C$_1$-C$_4$-alkoxycarbonyl, C$_1$-C$_4$-alkylaminocarbonyl, C$_1$-C$_4$-dialkylaminocarbonyl, C$_1$-C$_4$-alkylsulfinyl, C$_1$-C$_4$-alkylsulfonyl, C$_3$-C$_{10}$-cycloalkyl, phenyl which may itself have 1, 2, 3 or 4 substituents selected from halogen, C$_1$-C$_4$-alkyl, C$_1$-C$_4$-alkoxy, C$_1$-C$_4$-fluoroalkyl, C$_1$-C$_4$-alkyloxycarbonyl, trifluoromethylsulfonyl, formyl, nitro or cyano,
  C$_1$-C$_{20}$-haloalkyl, C$_2$-C$_{20}$-haloalkenyl, C$_2$-C$_{20}$-haloalkynyl, C$_3$-C$_{10}$-cycloalkyl, C$_5$-C$_{10}$-cycloalkenyl, heterocyclyl having from one to 3 heteroatoms selected from O, S and N, phenyl or naphthyl, where heterocyclyl, phenyl or naphthyl may themselves have 1, 2, 3 or 4 substituents selected from halogen, C$_1$-C$_4$-alkyl, C$_1$-C$_4$-alkoxy, C$_1$-C$_4$-fluoroalkyl, C$_1$-C$_4$-alkyloxycarbonyl, trifluoromethylsulfonyl, formyl, nitro or cyano,
R$^1$ and R$^2$ together may also form a saturated or partially unsaturated 5- to 8-membered nitrogen heterocycle which may itself be substituted by C$_1$-C$_4$-alkyl, C$_1$-C$_4$-alkoxy and/or C$_1$-C$_4$-haloalkyl, and have one or 2 carbonyl groups or thiocarbonyl groups and/or one or two further heteroatoms selected from O, S and N as ring members.

12. A process for preparing sulfuric diamides by reacting sulfamoyl halides of primary or secondary amines with ammonia, comprising the following steps:
  i) reacting a primary or secondary amine A1 with at least equimolar amounts of $SO_3$ or an $SO_3$ source in the presence of at least equimolar amounts of a tertiary amine A2, based in each case on the amine A1, and
  ii) reacting the reaction mixture obtained in step i) with at least the amount of a phosphorus halide required by the stoichiometry,
  iii) reacting the sulfamoyl halide obtained in step ii) with ammonia.

13. A process for preparing compounds of the general formula IV

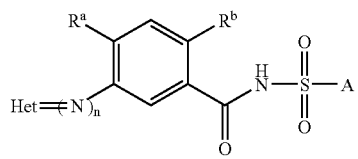

(IV)

where n is 0 or 1, Het is an optionally substituted 5- or 6-membered heterocycle which may have 1, 2 or 3 nitrogen atoms, optionally one further heteroatom selected from oxygen and sulfur, and optionally one or two carbonyl or thiocarbonyl groups as ring members, $R^a$ is hydrogen, fluorine or chlorine, $R^b$ is chlorine or cyano, and A is a radical derived from a primary or secondary amine A1, comprising the following steps:
  i) reacting a primary or secondary amine A1 with at least equimolar amounts of $SO_3$ or an $SO_3$ source in the presence of at least equimolar amounts of a tertiary amine A2, based in each case on the amine A1, to obtain an ammonium sulfamate;
  ii) reacting the ammonium sulfamate with at least the amount of a phosphorus halide required by the stoichiometry, to obtain a sulfamoyl halide of the amine A1;
  iii) reacting the sulfamoyl halide obtained in step ii) with ammonia to obtain a sulfamoyl amide; and
  iv) reacting the reaction product from step iii) with a compound of the general formula V

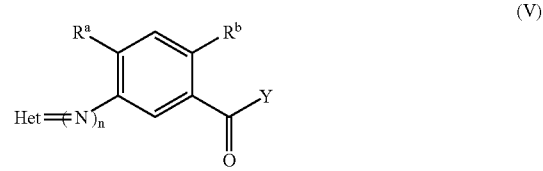

(V)

where Het, n, $R^a$ and $R^b$ are each as defined for formula IV and Y is OH, alkoxy or a halogen atom.

14. A process as claimed in claim 13, where n=0 and Het is a radical of the formula

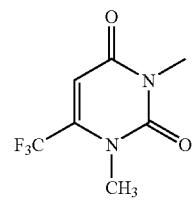

* * * * *